United States Patent [19]

Meek, deceased et al.

[11] Patent Number: Plant 5,326

[45] Date of Patent: Nov. 6, 1984

[54] CHRYSANTHEMUM PLANT NAMED VIKING

[75] Inventors: Jack M. Meek, deceased, late of Salinas, Calif.; by Saundra J. Meek, executrix, Canyon, Tex.; William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 435,692

[22] Filed: Oct. 21, 1982

[51] Int. Cl.[3] ..... A01H 5/00

[52] U.S. Cl. ..... Plt./79

[58] Field of Search ..... Plt./78-79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Viking having flat capitulum form, decorative capitulum type, bronze ray floret color, diameter across face of capitulum up to 75 mm., tall plant height, spreading branching pattern, average natural season flowering date of September 20, and average flowering response period of seven (7) weeks in photoperiodic controlled short day programs.

3 Drawing Figures

The present invention comprises a new and distinct cultivar of *Chrysanthemum morifolium,* Ramat., hereinafter referred to by the cultivar name Viking.

Viking is a product of a planned breeding program which had the objective of creating cultivars with decorative capitulum type, medium height, spreading branching pattern, durable inflorescence, seven (7) week flowering response period, and bronze ray floret color under outdoor natural season conditions.

Viking was originated from a cross made in a controlled breeding program planned and executed by Grace H. Mack in New Canaan, Conn. in the year 1976. The female parent was Y4080 a bronze decorative, an unnamed seedling from a cross of two unnamed seedlings (4570×859). The male parent was 414, a bronze decorative, an unnamed seedling from a cross of two unnamed seedlings (212×241).

Viking was discovered and selected as a flowering plant within the progeny of the stated cross by J. Michael Meek in 1977 in an outdoor field in Salinas, Calif. The first act of asexual reproduction of Viking was accomplished when vegetative cuttings were taken from the initial selection in 1977 in Salinas, Calif. by William E. Duffett.

Horticultural examination of selected units initiated 1978 has demonstrated that the combination of characteristics as herein disclosed for Viking are firmly fixed and are retained through successive generations of asexual reproduction.

Viking has not been observed under all possible environmental conditions. The phenotype may vary significantly with variations in environment such as temperature, light intensity, and day length. The following obsrvations, measurements, and comparisons describe plants grown in a field in Salinas, Calif.

Rooted cuttings were established in soil in one gallon containers maintained outdoors under the natural temperature and day length prevailing during July through September.

The following traits have been repeatedly observed and are determined to be basic characteristics of Viking which in combination distinguish this chrysanthemum as a new and distinctive cultivar:

(1) Flat capitulum form.

(2) Decorative capitulum type.

(3) Bronze ray floret color.

(4) Diameter across face of capitulum up to 75 mm.

(5) Tall plant height.

(6) Spreading branching pattern.

(7) Average natural season flowering date of September 20.

(8) Average flowering response period of seven (7) weeks in photoperiodic controlled flowering programs.

The accompanying photographic drawings show typical inflorescence and foliage characteristics of Viking. Sheet 1 is a color photograph of Viking. Sheet 2 is a black and white photograph showing three views of the inflorescence of Viking. Sheet 3 is a black and white photograph showing the leaves of Viking at three stages of growth (mature, intermediate and immature).

Of the many commercially available cultivars known to the present inventors, the most similar existing cultivar in comparison to Viking is the cultivar Ironsides, disclosed in U.S. Plant Pat. No. 3,896.

Reference is made to attached Chart A which compares certain characteristics of Viking with the same characteristics of Ironsides. It will be noted that in comparison to Ironsides, Viking has different ray floret color, later average natural season flower date, larger diameter across face of capitulum, taller plant height and more spreading branching pattern. The capitulum form and capitulum type of Viking are similar to those characteristics of Ironsides.

In the following description, color references are made to The Royal Horticultural Society Colour Chart. The color values were determined between 2:30 and 3:00 P.M. on Sept. 29, 1981 under 150 foot-candle light intensity at Salinas, Calif.

Botanical classification: *Chrysanthemum morifolium,* Ramat., cv Viking.

INFLORESCENCE

Capitulum:

*Form.*—Flat.

*Type.*—Decorative.

*Permanence.*—2 To 3 weeks.

*Diameter across face.*—60 To 75 mm.

Corolla of ray florets:

*Color (abaxial).*—Approximately 168A oxidizing to 167A, with 8A at base of ray.

*Color (adaxial).*—Approximately 168C streaked with 167A, with 10B at base of ray.

Reproductive organs:

*Androecium.*—Present disc florets.

*Gynoecium.*—Present both ray and disc florets.

Disc florets:

*Color.*—14A.

PLANT

General appearance: Spreading branching pattern; tall habit.

Foliage:

*Color (abaxial).*—Approximately 147A.

*Color (adaxial).*—Approximately 147B.

CHART A

COMPARISON OF VIKING AND IRONSIDES

| CULTIVAR | RAY FLORET COLOR | CAPITULUM FORM AND TYPE | AVERAGE NATURAL SEASON FLOWER DATE |
|---|---|---|---|
| VIKING | BRONZE | FLAT DECORATIVE | SEPTEMBER 20 |
| IRONSIDES | ORANGE BRONZE | FLAT DECORATIVE | SEPTEMBER 10 |

CHART A-continued

COMPARISON OF VIKING AND IRONSIDES

| CULTIVAR | PLANT HEIGHT | BRANCHING PATTERN AND SPREAD | DIAMETER ACROSS FACE OF CAPITULUM |
|---|---|---|---|
| VIKING | TALL | SPREADING | 60 to 75 mm. |
| IRONSIDES | MEDIUM | SEMI-UPRIGHT | 45 to 55 mm. |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., plant known by the name Viking, as described and illustrated, and particularly characterized as to uniqueness by the combined characteristics of flat capitulum form, decorative capitulum type, bronze ray floret color, diameter across face of capitulum up to 75 mm., tall plant height, spreading branching pattern, average natural season flowering date of September 20, and average flowering response period of seven (7) weeks in photoperiodic short day programs.

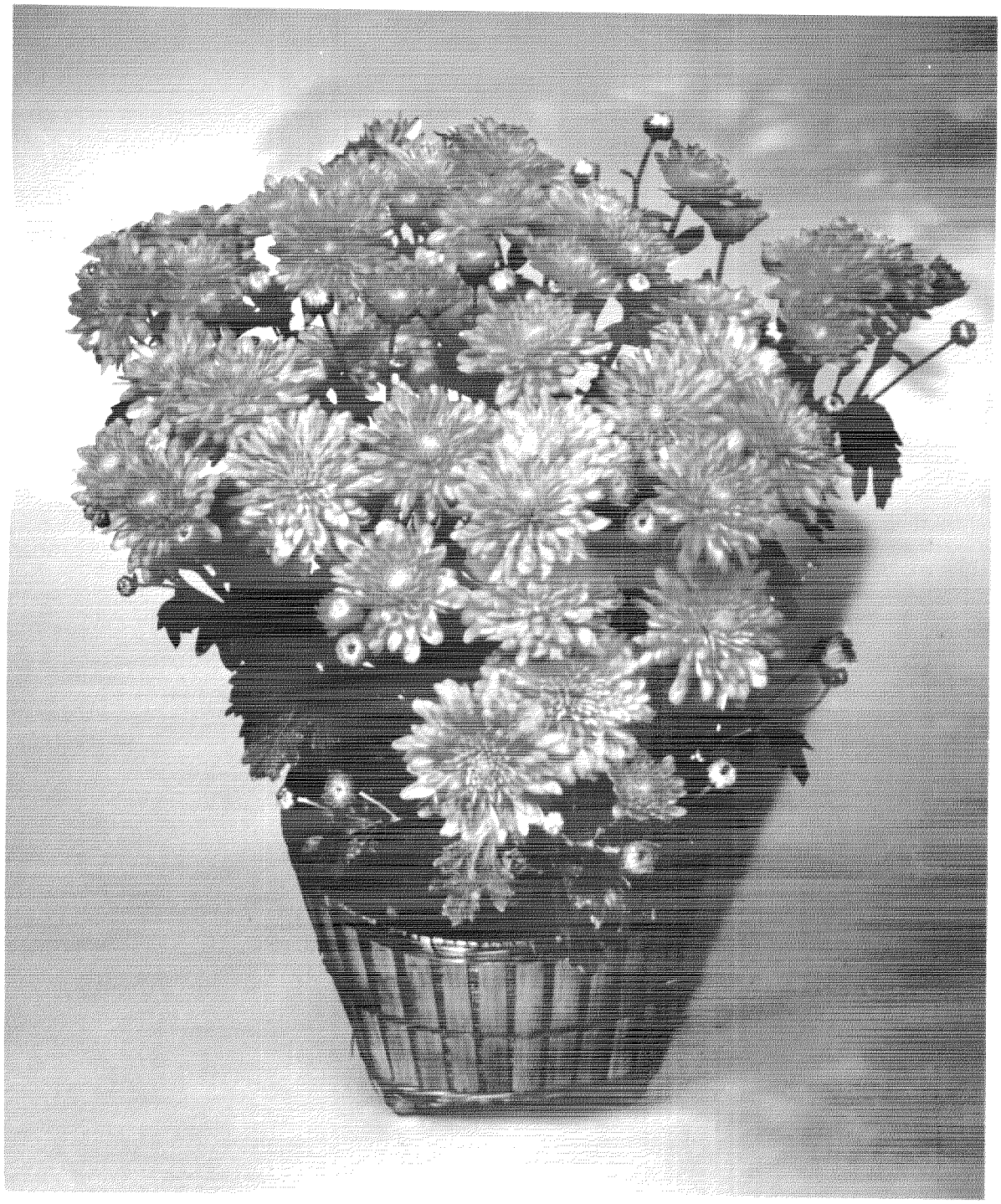

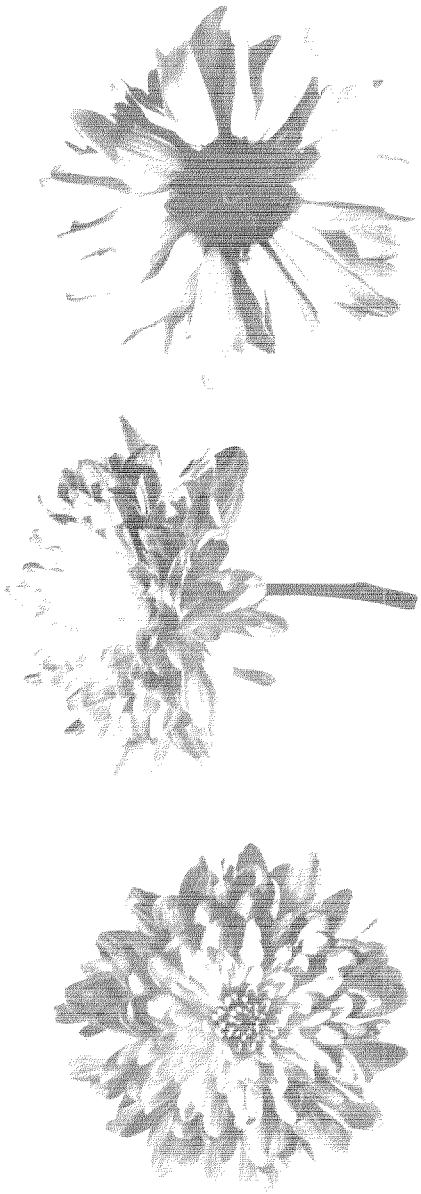

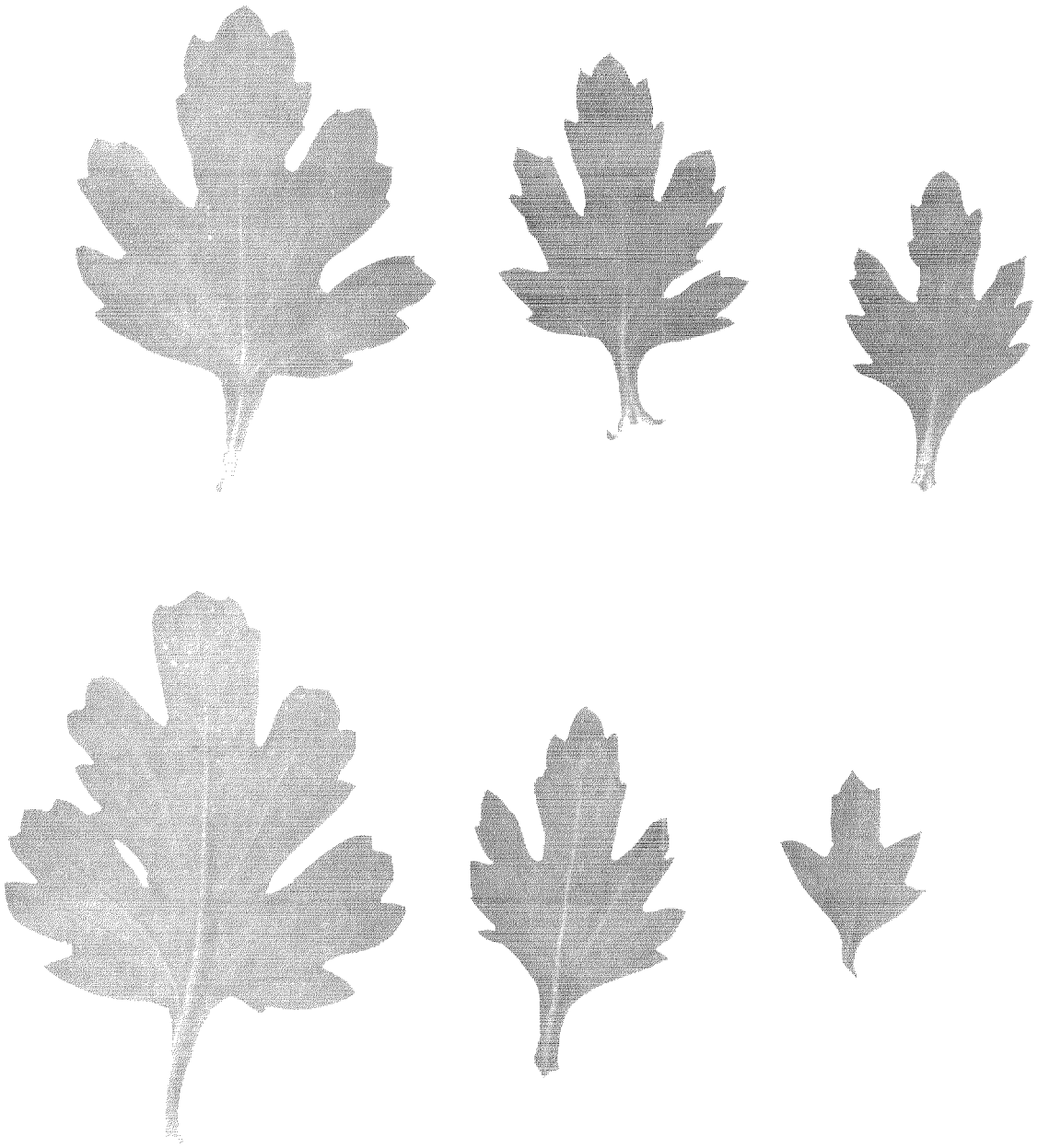

* * * * *